(12) United States Patent
El Gamal et al.

(10) Patent No.: US 8,709,788 B2
(45) Date of Patent: Apr. 29, 2014

(54) BIOLOGICAL ANALYSIS ARRANGEMENT AND APPROACH THEREFOR

(71) Applicant: The Board of Trustees of the Leland Stanford Junior University, Palo Alto, CA (US)

(72) Inventors: Abbas El Gamal, Palo Alto, CA (US); Helmy Eltoukhy, Woodside, CA (US); Khaled Salama, Stanford, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 13/680,796

(22) Filed: Nov. 19, 2012

(65) Prior Publication Data

US 2013/0078623 A1 Mar. 28, 2013

Related U.S. Application Data

(63) Continuation of application No. 12/323,645, filed on Nov. 26, 2008, now Pat. No. 8,313,904, which is a continuation of application No. 10/663,935, filed on Sep. 16, 2003, now Pat. No. 7,595,883.

(60) Provisional application No. 60/411,286, filed on Sep. 16, 2002.

(51) Int. Cl.
| | |
|---|---|
| C12M 1/00 | (2006.01) |
| C12M 1/34 | (2006.01) |
| C12M 3/00 | (2006.01) |
| G01N 1/10 | (2006.01) |
| G01N 21/00 | (2006.01) |
| G01N 27/00 | (2006.01) |
| C07H 21/02 | (2006.01) |
| C07H 21/04 | (2006.01) |

(52) U.S. Cl.
USPC ... 435/283.1; 435/6.1; 435/287.1; 435/287.2; 356/246; 356/440; 422/82.01; 422/82.05; 536/23.1; 536/24.3

(58) Field of Classification Search
USPC .......... 435/6.1, 283.1, 287.1, 287.2; 356/246, 356/440; 422/82.01, 82.05; 536/23.1, 24.3
See application file for complete search history.

(56) References Cited

U.S. PATENT DOCUMENTS

| | | | |
|---|---|---|---|
| 4,499,052 A | 2/1985 | Fulwyler | |
| 4,822,746 A | 4/1989 | Walt | |
| 4,841,348 A | 6/1989 | Shizukuishi et al. | |
| 4,971,903 A | 11/1990 | Hyman | |
| 5,073,029 A | 12/1991 | Eberly et al. | |
| 5,105,305 A | 4/1992 | Betzig et al. | |
| 5,114,864 A | 5/1992 | Walt | |
| 5,143,853 A | 9/1992 | Walt | |
| 5,244,636 A | 9/1993 | Walt et al. | |
| 5,244,813 A | 9/1993 | Walt et al. | |
| 5,250,264 A | 10/1993 | Walt et al. | |
| 5,252,494 A | 10/1993 | Walt | |
| 5,254,477 A | 10/1993 | Walt | |
| 5,298,741 A | 3/1994 | Walt et al. | |
| 5,320,814 A | 6/1994 | Walt et al. | |
| 5,357,590 A | 10/1994 | Auracher | |
| 5,396,198 A | 3/1995 | Yamashita et al. | |
| 5,461,425 A | 10/1995 | Fowler et al. | |
| 5,481,629 A | 1/1996 | Tabuchi | |
| 5,494,798 A | 2/1996 | Gerdt et al. | |
| 5,496,997 A | 3/1996 | Pope | |
| 5,512,490 A | 4/1996 | Walt et al. | |
| 5,547,839 A | 8/1996 | Dower et al. | |
| 5,571,639 A | 11/1996 | Hubbell et al. | |
| 5,575,849 A | 11/1996 | Honda et al. | |
| 5,603,351 A | 2/1997 | Cherukuri et al. | |
| 5,605,662 A | 2/1997 | Heller et al. | |
| 5,633,972 A | 5/1997 | Walt et al. | |
| 5,639,603 A | 6/1997 | Dower et al. | |
| 5,795,716 A | 8/1998 | Chee | |
| 5,807,522 A | 9/1998 | Brown et al. | |
| 5,814,524 A | 9/1998 | Walt et al. | |
| 5,824,477 A | 10/1998 | Stanley | |
| 5,840,256 A | 11/1998 | Demers et al. | |

(Continued)

FOREIGN PATENT DOCUMENTS

| | | |
|---|---|---|
| EP | 0 478 319 A1 | 4/1992 |
| EP | 0 799 897 B1 | 11/1998 |

(Continued)

OTHER PUBLICATIONS

Abel, "Fiber-Optic Evanescent Wave Biosensor for the Detection of Oligonucleotides", Analytical Chemistry, vol. 68, Sep. 1996, pp. 2905-2912.

(Continued)

Primary Examiner — Narayan Bhat
(74) Attorney, Agent, or Firm — Crawford Maunu PLLC

(57) ABSTRACT

Characteristics of a chemical or biological sample are detected using an approach involving light detection. According to an example embodiment of the present invention, an assaying arrangement including a light detector is adapted to detect light from a sample, such as a biological material. A signal corresponding to the detected light is used to characterize the sample, for example, by detecting a light-related property thereof. In one implementation, the assaying arrangement includes integrated circuitry having a light detector and a programmable processor, with the light detector generating a signal corresponding to the light and sending the signal to the processor. The processor provides an output corresponding to the signal and indicative of a characteristic of the sample.

18 Claims, 8 Drawing Sheets

(56) References Cited

U.S. PATENT DOCUMENTS

| | | | |
|---|---|---|---|
| 5,843,767 A | 12/1998 | Beattie | |
| 5,849,486 A | 12/1998 | Heller et al. | |
| 5,854,684 A | 12/1998 | Stabile et al. | |
| 5,863,708 A | 1/1999 | Zanzucchi et al. | |
| 5,866,321 A | 2/1999 | Matsue et al. | |
| 5,900,481 A | 5/1999 | Lough et al. | |
| 5,902,723 A | 5/1999 | Dower et al. | |
| 5,942,775 A | 8/1999 | Yiannoulos | |
| 5,965,452 A | 10/1999 | Kovacs | |
| 6,023,540 A | 2/2000 | Walt et al. | |
| 6,040,138 A | 3/2000 | Lockhart et al. | |
| 6,045,996 A | 4/2000 | Cronin et al. | |
| 6,051,380 A | 4/2000 | Sosnowski et al. | |
| 6,083,763 A | 7/2000 | Balch | |
| 6,085,576 A | 7/2000 | Sunshine et al. | |
| 6,096,496 A | 8/2000 | Frankel | |
| 6,099,803 A | 8/2000 | Ackley et al. | |
| 6,124,102 A | 9/2000 | Fodor et al. | |
| 6,150,189 A | 11/2000 | Pan | |
| 6,150,683 A | 11/2000 | Merrill et al. | |
| 6,200,737 B1 | 3/2001 | Walt et al. | |
| 6,210,891 B1 | 4/2001 | Nyren et al. | |
| 6,210,910 B1 | 4/2001 | Walt et al. | |
| 6,222,619 B1 | 4/2001 | Herron et al. | |
| 6,258,568 B1 | 7/2001 | Nyren | |
| 6,274,320 B1 | 8/2001 | Rothberg et al. | |
| 6,287,776 B1 | 9/2001 | Hefti | |
| 6,310,571 B1 | 10/2001 | Yang et al. | |
| 6,325,977 B1 * | 12/2001 | Theil | 422/82.05 |
| 6,327,410 B1 | 12/2001 | Walt et al. | |
| 6,379,897 B1 | 4/2002 | Weidenhammer et al. | |
| 6,380,880 B1 | 4/2002 | Bidermann | |
| 6,399,365 B2 | 6/2002 | Besemer et al. | |
| 6,416,952 B1 | 7/2002 | Pirrung et al. | |
| 6,429,027 B1 | 8/2002 | Chee et al. | |
| 6,440,722 B1 | 8/2002 | Knapp et al. | |
| 6,458,547 B1 * | 10/2002 | Bryan et al. | 506/9 |
| 6,482,593 B2 | 11/2002 | Walt et al. | |
| 6,491,871 B1 | 12/2002 | Fodor et al. | |
| 6,518,085 B1 | 2/2003 | Wang et al. | |
| 6,544,732 B1 | 4/2003 | Chee et al. | |
| 6,544,739 B1 | 4/2003 | Fodor et al. | |
| 6,576,424 B2 | 6/2003 | Fodor et al. | |
| 6,597,000 B2 | 7/2003 | Stern | |
| 6,600,031 B1 | 7/2003 | Fodor et al. | |
| 6,610,482 B1 | 8/2003 | Fodor et al. | |
| 6,617,565 B2 | 9/2003 | Wu | |
| 6,646,243 B2 | 11/2003 | Pirrung et al. | |
| 6,650,411 B2 | 11/2003 | Odoy et al. | |
| 6,686,150 B1 | 2/2004 | Blackburn et al. | |
| 6,784,982 B1 | 8/2004 | Blumenfeld et al. | |
| 6,791,611 B2 | 9/2004 | Yang | |
| 6,825,927 B2 | 11/2004 | Goldman et al. | |
| 6,828,100 B1 | 12/2004 | Ronaghi | |
| 6,841,128 B2 | 1/2005 | Kambara et al. | |
| 7,061,595 B2 | 6/2006 | Cabuz et al. | |
| 7,122,408 B2 | 10/2006 | Mouli et al. | |
| 7,145,645 B2 | 12/2006 | Blumenfeld et al. | |
| 7,163,822 B2 | 1/2007 | Yazawa et al. | |
| 7,323,305 B2 | 1/2008 | Leamon et al. | |
| 7,595,883 B1 | 9/2009 | El Gamal et al. | |
| 2001/0029049 A1 | 10/2001 | Walt et al. | |
| 2001/0055801 A1 | 12/2001 | Chen et al. | |
| 2002/0004204 A1 | 1/2002 | O'Keefe | |
| 2002/0051971 A1 | 5/2002 | Stuelpnagel et al. | |
| 2002/0102578 A1 | 8/2002 | Dickinson et al. | |
| 2002/0131899 A1 | 9/2002 | Kovacs | |
| 2002/0132221 A1 | 9/2002 | Chee et al. | |
| 2003/0068629 A1 | 4/2003 | Rothberg et al. | |
| 2003/0082571 A1 | 5/2003 | Kachab et al. | |
| 2003/0108867 A1 | 6/2003 | Chee et al. | |
| 2003/0157499 A1 | 8/2003 | Lundeberg et al. | |
| 2003/0162217 A1 | 8/2003 | Rothberg et al. | |
| 2003/0235924 A1 | 12/2003 | Adams et al. | |
| 2004/0197793 A1 | 10/2004 | Hassibi et al. | |
| 2005/0046847 A1 | 3/2005 | Cromwell et al. | |
| 2005/0130173 A1 | 6/2005 | Leamon et al. | |
| 2007/0024728 A1 | 2/2007 | Muramatsu et al. | |
| 2007/0140912 A1 | 6/2007 | Minot et al. | |

FOREIGN PATENT DOCUMENTS

| | | |
|---|---|---|
| EP | 1 309 729 B1 | 12/2004 |
| WO | 93/23564 A1 | 11/1993 |
| WO | 97/40385 A1 | 10/1997 |
| WO | 98/13523 A1 | 4/1998 |
| WO | 98/28440 A1 | 7/1998 |
| WO | 98/40726 A1 | 9/1998 |
| WO | 98/50782 A2 | 11/1998 |
| WO | 98/53093 A1 | 11/1998 |
| WO | 99/18434 A1 | 4/1999 |
| WO | 99/27140 A1 | 6/1999 |
| WO | 99/45357 A2 | 9/1999 |
| WO | 99/67641 A2 | 12/1999 |
| WO | 00/09738 A1 | 2/2000 |
| WO | 00/13004 A2 | 3/2000 |
| WO | 00/16101 A2 | 3/2000 |
| WO | 00/39587 A1 | 7/2000 |
| WO | 00/43552 A2 | 7/2000 |
| WO | 00/47996 A2 | 8/2000 |
| WO | 00/48000 A1 | 8/2000 |
| WO | 00/56934 A1 | 9/2000 |
| WO | 00/63437 A2 | 10/2000 |
| WO | 00/71243 A1 | 11/2000 |
| WO | 00/71992 A1 | 11/2000 |
| WO | 00/71995 A2 | 11/2000 |
| WO | 00/75373 A2 | 12/2000 |
| WO | 01/06012 A1 | 1/2001 |
| WO | 02/12897 A2 | 2/2002 |

OTHER PUBLICATIONS

Barnard, "A Fibre-Optic Chemical Sensor with Discrete Sensing Sites", Nature, vol. 353, (Sep. 1991), pp. 338-340.

Walt, "Fiber-Optic Sensors for Continuous Clinical Monitoring", Proc. IEEE, 80(6), (1992), pp. 903-911.

Walt, "Fiber-Optic Imaging Sensors", Accounts of Chemical Research, 31(5), (1998), pp. 267-278.

Walt, et al., "Design, Preparation, and Applications of Fiber-Optic Chemical Sensors for Continuous Monitoring", Fiber Optic Chemical Sensors, Chemical Sensors and Microinstrumentation, (1989), pp. 252-272.

Strachan, "A Rapid General Method for the IDentification of PCR Products Using a Fibre-Optic Biosensor and its Application to the Detection of Listeria", Letters in Applied Microbiology, 21, vol. 21. No. 1, (Jul. 1995) pp. 5-9.

Smith, et al., "Fluorescence Detection in Automated DNA Sequence Analysis", Nature, 321, (1986) pp. 674-679.

Butte, "The Use and Analysis of Microarray Data", Nature Reviews Drug Discovery, 1, (2002) pp. 951-960.

Cunin, "Biomolecular Screening with Encoded Porous-Silicon Photonic Crystals", Nature Materials, 1, (2002) pp. 39-41.

Zhujun, et al., "A Fluorescence Sensor for Quantifying pH in the Range from 6.5 to 8.5", Analytica Chimica Acta vol. 160, (1984) pp. 47-55.

Peterson, et al., "Fiber-Optic Sensors for Biomedical Applications", Science, vol. 13, Apr. 1984, 123-127.

Peterson, J I., et al., "Fiber Optic pH Probe for Physiological Use.", Analytical Chemistry., v52.,No. 6. May 1980, 864-869.

Healey, B. G., et al., "Fiber Optic DNA Sensory Array Capable of Detecting Point Mutations", Analytical Biochemistry, v. 251., No. 2 (1997), 270-279.

Munkholm, C. et al., "Polymer modification of fiber optical imaging fibers", Analytical Chemistry vol. 58 Jun. 1986, vol. 58 No. 7, 1427-1430.

Pease, et al., "Light-generated oligonucleotide array for rapid DNA sequence analysis", Proc. Natl. Acad. Sci., 1994. p. 5502-5026, vol. 91, Issue 11, USA.

Stimpson, et al., "Real-time detection of DNA hybridization and melting on oligonucleotide arrays on glass supports", Nucleic Acids Res., 1994, p. 5456-5465, vol. 22, Oxford, England.

(56) References Cited

OTHER PUBLICATIONS

Ahmadian, et al., Biotechniques; 28(1) 140-4, 146-7,(Jan. 2000).
Barshop, et al., "Luminescent immobilized enzyme test systems for inorganic pyrophosphate:assays using firefly luciferase and nicotinamide-mononucleotide adenylyl transferase or adenosine-5'-triphosphate sulfurylase", Anal. Biochem. 197(1) 266-272 (1991).
Cook, et al., "A rapid Enzymatic Assay for Measurement of Inorganic Pyrophosphate in Animal Tissues", Anal. Biochem. 91:557 1978.
Drake, H. L., et al., "A new, convenient method for the rapid analysis of inorganic pyrophosphate", Anal. Biochem. 94:117 (1979).
Johnson, et al., "An Enzymatic method for determination of inorganic pyrophosphate and its use as an assay for RNA polymerase", Anal. Biochem. 26:137 (1968).
Justesen, et al., "Spectrophotometric Pyrophosphate Assay of 2', 5'-Oligoadenylate Synthetase", Anal. Biochem. 207 (1):90-93 (1992).
Karamohamed and Nyren, et al., "Real-Time detection and quantification of adenosine triphosphate sulfurylase activity by a bioluminometric approach", Anal. Biochem. 271:81-85 (1999).
Lust, et al., "A rapid enzymatic assay for measurement of inorganic pyrophsophate in biological samples", Clin. Chem. Acta 66 (2):241 (1976).
Nyren, et al., "Detection of Single-Base Changes Using a Bioluminometric Primer Extension Assay", Anal. Biochem. Jan. 15, 1997; 244 (2) 367-73.
Nyren, "Apyrase Immobilized on Paramagnetic Beads Used to Improve Detection Limits in Bioluminometric ATP monitoring", J. Biolumin Chemilumin. Jan.-Feb. 1994; 9 (1):29-34.
Nyren, et al., "Solid Phase DNA Minisequencing by an Enzymatic Luminometric Inorganic Phyrophosphate Detection Assay", Anal Biochem. Jan. 1993; 208 (1):171-5.
Nyren, P. et al., "Enzymatic method for continuous monitoring of inorganic pyrophosphate synthesis", Anal. Biochem. 151:504-509(1985).
Ronaghi, et al., "Analyses of Secondary Structures in DNA by Pyrosequencing", Anal. Biochem. Feb. 1, 1999; 267 (1):65-71.
Ronaghi, M et al., "Real-time DNA sequencing using detection of pyrophosphate release", Anal. Biochem. Nov. 1, 1996; 242 (1):84-89.
Walt, D "Bead Based Fiber-Optic Arrays", Science. 287:451-452 (1999).
Sabanayagam, et al., "Molecular DNA Switches and DNA chips", SPIE:Progress in Biomedical Optics, Jan. 1999 pp. 90-97, vol. 3606.
Koster, H et al., "A strategy for rapid and efficient DNA sequencing by mass spectrometry", Nature Biotechnology, Sep. 1996, pp. 1123-1128, vol. 14.
Hyman, E D., "A new method of sequencing DNA", Anal. Biochem, 1988, pp. 423-436, vol. 174.
Johnson, K. A., et al., "Continuous assay for DNA polymerization by light scattering", Anal. Biochem., 1984, pp. 192-194, vol. 136.
Chee, M et al., "Enzymatic multiplex DNA sequencing", Nucl. Acid Res., 1991, pp. 3301-3305 vol. 19 No. 12.
Reeves, R. E., et al., "Enzymic assay method for inorganic pyrophosphate", Anal. Biochem. 1969, pp. 282-287, vol. 28.
Margulies, Marcel et al., "Genome Sequencing in microfabricated high-density picolitre reactors", Nature, vol. 437 No. 7057,(Jul. 31, 2005), 376-380.
Dickinson, et al., "Generating Sensor Diversity Through Combinatorial Polymer Synthesis", Analytical Chemistry, vol. 69(17), (1997), 97-107.
Ferguson, J A., et al., "A Fiber-Optic DNA Biosensor Microarray for the Analysis of Gene Expression", Nature Biotechnol.vol. 14 (1996), 1681-1684.
Fodor, "Light-Directed, Spatially Addressable Parallel Chemical Synthesis", Science, vol. 251, (1991), 767-773.

Fuh, "Single Fibre Optic Fluorescense pH Probe", Analyst, vol. 112, (1987), 1159-1163.
Healey, "Improved Fiber-Optic Chemical Sensor for Penicillin", Analytical Chemistry, vol. 67(24), (Dec. 15, 1995), 4471-4476.
Hirschfeld, "Laser-Fiber-Optic "Optrode" for Real Time in Vivo Blood Carbon Dioxide Level Monitoring", Journal of Lightwave Technology, vol. LT-5(7), (1987), 1027-1033.
Lippitsch, et al., "Fibre-Optic Oxygen Sensor with the Fluorescence Decay Time as the Information Carrier", Analytical Chemistry Acta, vol. 205 (1998), 1-6.
Lubbers, et al., "Optical Fluorescense Senosrs for Continuous Measurement of Chemical Concentrations if Biological Systems", Sens. Actuators, vol. 4, (1983), 641-654.
Michael, "Fabrication of Micro- and Nanostructures Using Optical Imaging Fibers and Their Use as Chemical Sensors", Proc. 3rd Intl Symp, Microstructures and Microfabricated Systems, (1997), 152-157.
Michael, "Making Sensors out of Disarray: Optical Sensor Microarrays", Proc. SPIE, vol. 3270, (1998), 34-41.
Michael, "Randomly Ordered Addressable High-Density Optical Sensor Arrays", Analytical Chemistry, vol. 70(7), (1998), 1242-1248.
Mignani(Grazia), "In-Vivo Biomedical Monitoring by Fiber-Optic Systems", Journal of Lightwave Technology, vol. 13(7), (1995),1396-1406.
Milanovich, et al., "Clinical Measurements Using Fiber Optics and Optrodes", Novel Optical Fiber Techniques for Medical Application, SPIE, vol. 494, (1984), 1831.
Munkholm, et al., "A Fiber-Optic Sensor for CO2 Measurement", Talanta, vol. 35(2), (1988), 109-112. Pantano, "Ordered Nanowell Arrays", Chem Mater, vol. 8(12), (1996), 2832-2835.
Pantano, et al., "Analytical Applications of Optical imaging Fibers", Analytical Chemistry, 67, (1995), 481A-487A.
Piunno, "Fiber-Optic DNA Sensor for Fluorometric Nubleic Acid Determination", Analytical Chemistry, 67, vol. 67. No. 15 Aug. 1995, 2635-2643.
Pope, "Fiber Optic Chemical Microsensors Employing Optically Active Silica Microspheres", SPIE, 2388, (1995), 245-256.
Ronaghi, M et al., "A Sequencing Method Based on Real-Time Phyrophosphate", Science. Jul. 17, 1998; 281 (5375):363-365.
Saari, et al., "pH Sensor Based on Immobilizied Fluoresceinamine", Analytical Chemistry, 54, vol. 54. No. 4 (Apr. 1982), 821-823.
Seitz, et al., "Chemical Sensors Based on Immobilized Indicators and Fiber Optics", CRC Critical Reviews in Analytical Chemistry, 19(2), (1988), 135-173.
Seitz, "Chemical Sensors Based on Fiber Optics", Analytical Chemistry, 56(1), (Jan. 1984), 16A-34A.
Wolfbeis, "Fiber Optical Fluorosensors in Analytical and Clinical Chemistry", Molecular Luminescence Spectroscopy, Methods and Applications (S.G. Schulman, editor), Wiley & Sons, New York, (1988), 129-280.
Wolfbeis, et al., "Fiber-Optic Fluorosensor for Oxygen and Carbon Dioxide", Analytical Chemistry, 60, (1988),2028-2030.
Chamberlain, Savvas G., "Photosensitivity and Scanning of Silicon Image Detector Arrays", IEEE Journal of Solid-State Circuits, vol. SO-4, No. 6, Dec. 1969.
Noble, Peter J., "Self-Scanned Silicon Image Detector Arrays", IEEE Transactions on Electron Devices, vol. Ed. 15, No. 4, Apr. 1968.
Pantano, "Ordered Nanowell Arrays", Chem Mater, vol. 8(12), (1996), 2832-2835.

* cited by examiner

BIOLOGICAL ANALYSIS ARRANGEMENT AND APPROACH THEREFOR

RELATED PATENT DOCUMENTS

This patent document is a continuation under 35 U.S.C. §120 of U.S. patent application Ser. No. 12/323,645 filed on Nov. 26, 2008 (U.S. Pat. No. 8,313,904); which is further a continuation of U.S. patent application Ser. No. 10/663,935 filed on Sep. 16, 2003 (U.S. Pat. No. 7,595,883), which claims benefit of U.S. Provisional Patent Application Ser. No. 60/411,286 filed Sep. 16, 2002 and entitled "Platform For Biological Studies," which are incorporated herein by reference.

FIELD OF THE INVENTION

The present invention relates generally to biological analysis, and more particularly to arrangements and approaches for analyzing biological samples.

BACKGROUND

The detection of biological species within complex systems is important for many applications. Among these many applications, biomedical and environmental applications show perhaps the most immediate benefit, for example, with respect to infectious disease identification, medical diagnostics and therapy, biotechnology, animal husbandry, and genetic plant engineering.

A variety of sensing schemes have been developed for molecular detection, including approaches such as electrochemical, optical absorption, interferometric sensing, and fluorescence sensing. In addition, there are several methods for selectively identifying biological species, including antibody detection and assay (i.e., analysis to detect the presence, absence or quantity of a molecule) using molecular hybridization techniques. Assaying approaches including, e.g., Enzyme-linked Immunosuppresent Assays or ELISA are often used in this manner. Joining a single strand of nucleic acid with a complementary probe sequence is known as hybridization, or incorporation.

Generally, to identify sequence-specific nucleic acid segments, sequences complementary to those segments are designed to create a specific probe for a target cell, such as a pathogen or mutant cell. Nucleic acid strands tend to pair with their complements to form double-stranded structures. Thus, a single-stranded DNA molecule (e.g., a probe), in a complex mixture of DNA containing large numbers of other nucleic acid molecules, will seek out its complement (e.g., a target). In this manner, incorporation provides an accurate way to identify very specific DNA sequences, such as gene sequences from bacteria or viral DNA. Factors impacting the incorporation or re-association of two complementary DNA strands include temperature, contact time, salt concentration, degree of mismatch between the pairs, and the length and concentration of the target and probe sequences.

Pyrosequencing is an assaying approach that is widely used in biotechnology applications for real-time sequencing by synthesis that takes advantage of coupled enzymatic reactions to monitor DNA synthesis. Pyrosequencing offers accurate and consistent analysis of large numbers of short to medium length DNA sequences, and compatibility with standard biochemical reactions, such as polymerase chain reaction (PCR). For example, separation technologies such as capillary array electrophoresis and micro-array technology use pyrosequencing for the detection of analytes such as DNA and proteins. In the presence of a primed DNA template, DNA polymerase incorporates a nucleotide if the nucleotide is complimentary to the target DNA. As a result of incorporation, a pyrophosphate (PPi) molecule is released and consequently detected by a pair of coupled enzymatic reactions, culminating in the generation of light by firefly luciferase. The excess (unreacted) nucleotides are enzymatically removed in real-time, typically using apyrase.

In one approach, pyrosequencing involves first hybridizing a sequencing primer to a single stranded, PCR amplified, DNA template. The DNA template is then incubated with enzymes such as DNA polymerase, ATP sulfurylase, luciferas and apyrase, along with substrates adenosine 5' phosphosulfate (APS) and luciferin. Thereafter, deoxyribonucleotide triphosphate (dNTP) is added to the reaction. DNA polymerase catalyzes the dNTP into the DNA strand if it is complementary to the base in the template strand, with each incorporation occurrence being accompanied by an equimolar release of PPi to the amount of incorporated nucleotide. In the presence of APS, ATP sulfurylase converts PPi to ATP. In turn, this ATP, mediated by the luciferase, drives the conversion of luciferin to oxyluciferin generating light in the visible spectrum in amounts proportional to the amount of ATP consumed. The characteristics of the light are observable as an indication of the quantity of nucleotides incorporated. Apyrase continuously degrades ATP and any unincorporated dNTP to eventually terminate the light generation and regenerate the reaction so that other dNTPs can be added, one at a time, to the mixture. The complimentary DNA strand is built up, and detected through light indications, as the process continues. Conventional biological assays using approaches including those discussed above, however, are highly repetitive, can be labor intensive and are typically performed with microliter volume samples. The associated biochemical procedures comprising these protocols often require days or weeks to perform at a cost of hundreds of dollars per test. For instance, performing biological assays involving the detection of characteristics of a biologically active substance using an in vivo or in vitro tissue or cell model under controlled conditions can be tedious. Problems remain in reproducibly detecting and measuring low levels of biological compounds conveniently, safely and quickly. Furthermore, there continues to be a need for portable, low-power and low-cost designs that can operate robustly at various temperatures from below zero to room temperature thereby accommodating several different chemistries and applications.

SUMMARY

The present invention is generally directed to an approach for micro detection/analysis of various molecule types, such as biological species, in a manner that addresses the aforementioned issues, as well as other related issues. The present invention is exemplified in a number of implementations and applications, some of which are summarized below.

In one example embodiment of the present invention, a light-responsive sampling circuit on a substrate is adapted to detect optical characteristics of a biological sample. The light-responsive sampling circuit includes a light detector and a processor. The light detector generates a signal in response to light received from the biological sample (e.g., reflected light) and the processor receives the signal. The processor processes the generated signal to provide an indication of a characteristic of the biological sample related to the reflected light (e.g., to identify structure and/or composition of the biological sample). With this approach, inexpensive and portable biosensing is realized to selectively identify target compounds and assay large numbers of samples inexpensively for detection including environmental and biomedical diagnostics.

According to another example embodiment of the present invention, a microcircuit arrangement includes a sample preparation structure, and an assay, detection, data processing and analysis circuit arrangement at least partially fabricated on a common integrated circuit chip substrate. This microcircuit arrangement is readily implemented for detecting excitable target markers, e.g., in applications such as biological assays.

In another example embodiment of the present invention, a microcircuit arrangement includes an imager, such as a CCD or IGFET-based (e.g., CMOS-based) imager and an ultrasonic sprayer for nucleotide and enzyme/reagent delivery. The imager has an imaging plane, and reactant slides are arranged directly above the imaging plane to simulate the physical parameters associated with assaying a biological sample using a microcircuit arrangement. In one particular implementation, the microcircuit arrangement is constructed without optics for light detection.

Other example aspects of the present invention are directed to methods and systems for manufacturing integrated circuits for such assay, detection, data processing and analysis approaches as discussed above. These methods and systems are implemented using a variety of approaches that are a function of types of target samples and needed sensitivity for the particular analysis being performed.

These above-characterized aspects, as well as other aspects, of the present invention are exemplified in a number of illustrated implementations and applications, some of which are shown in the figures and characterized in the claims section that follows. However, the above summary is not intended to describe each illustrated embodiment or every implementation of the present invention.

BRIEF DESCRIPTION OF THE DRAWINGS

The invention may be more completely understood in consideration of the detailed description of various embodiments of the invention that follows in connection with the accompanying drawings, in which.

Figure 1:
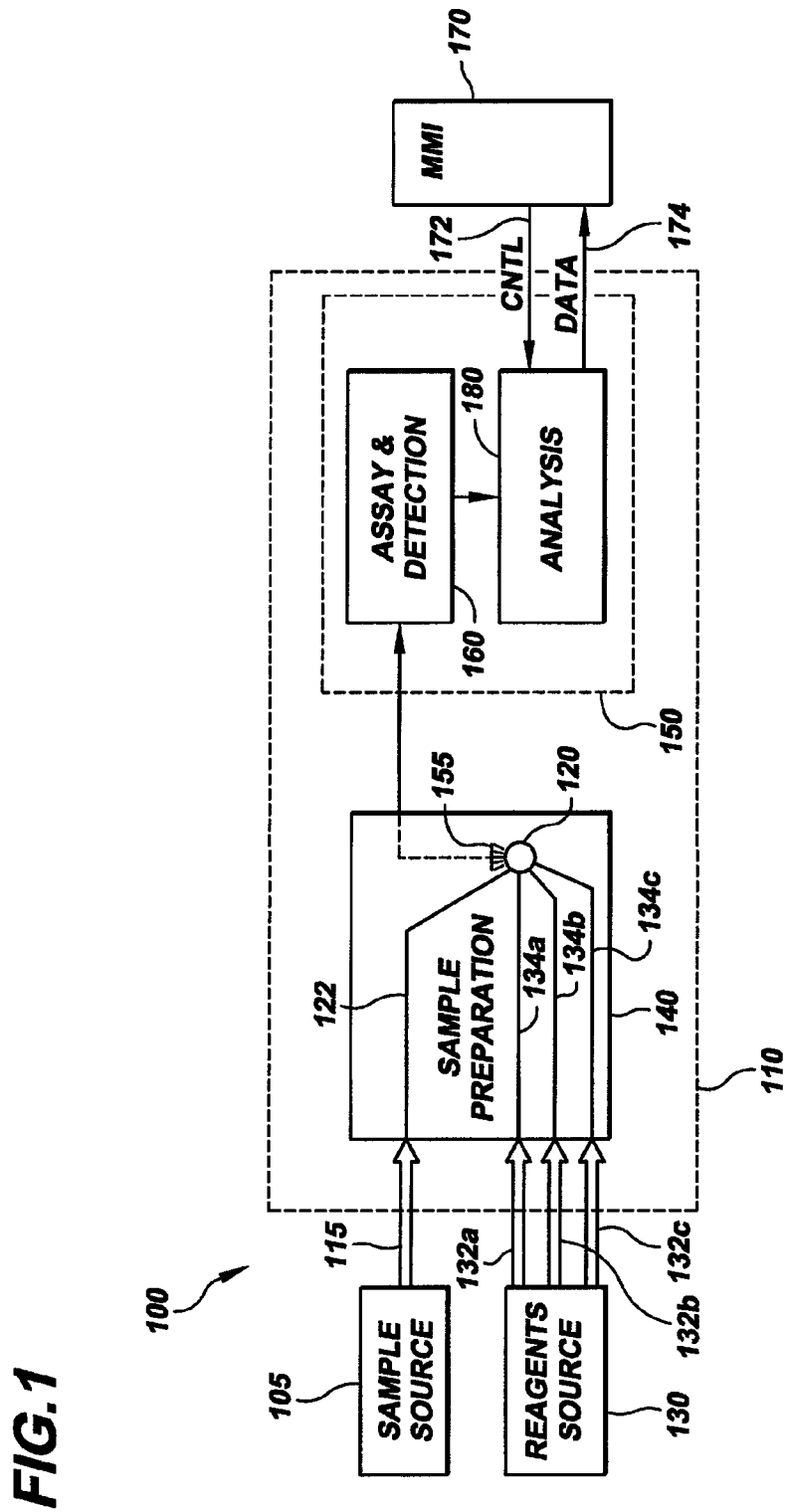
FIG. 1 is a block diagram illustrating a microcircuit arrangement, according to an example embodiment of the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The present invention is believed to be applicable to a variety of different types of devices, approaches and manufacturing methods. The invention has been found to be particularly suited for applications directed to an integrated microcircuit arrangement adapted to detect/analyze various types of molecules. One such example application is specifically directed to detecting/analyzing biological species using luminescence detection. Another such example application is specifically directed to detecting/analyzing biological species using pyrosequencing sensing. While the present invention is not necessarily limited to such applications, various aspects of the invention may be appreciated through a discussion of various examples using this context.

One aspect of the present invention is directed to an integrated microchip biosensor device. The device employs multiple optical (e.g., photo) sensing elements (detection components) and processing microelectronics on a single integrated chip adapted to image (i.e., capture light from) a sample. The device is used in conjunction with a sample structure having one or more nucleic acid-based bioreceptors designed to detect sequence specific genetic constituents in complex samples. The microchip devices of the present invention combine integrated circuit elements, electro-optics, and detection components in a self-contained, integrated microcircuit arrangement having a single-sided operating architecture. Nucleic acid-based receptor probes are typically included in a biochip containing a biological sample. According to various implementations of the present invention, the device may incorporate one or more biochips for presenting/processing the biological sample, or the sensing apparatus may be made portable to operate upon biochips that are independent from the device. The architectures of the present invention essentially couple the optoelectronic sensing and the data processing therefrom, on a single chip platform. This is advantageous for applications where a disposable assaying chip is desirable.

The integrated biosensor device discussed above, as well as the other light-sensing arrangements discussed herein, is adaptable for use in connection with a variety of sample types and detection approaches, including those discussed in the background above. For instance, DNA can be sequenced using an approach similar to that discussed above for generating light, with the integrated biosensor device using the generated light to detect light characteristics that are attributable to certain DNA sequences. The detection of single nucleotide polymorphisms (SNPs), which are common DNA sequence variations among individuals, can also be carried out using the integrated biosensor for comparative sequencing purposes. For example, SNP detection can be achieved using the integrated biosensor to comparatively sequence single base DNA pairs (the smallest building block of DNA) from different individuals. Pathogens can be detected and quantified with the integrated biosensor, for example, using luciferase-based immunoassays and associating detected light with particular pathogens and quantities thereof. DNA strands can be quantified for gene expression using the integrated biosensor to detect light characteristics that are correlated to the quantity of DNA strands. In addition, disease and trait inheritance can be tracked within family and other groups using light detection with the integrated biosensor to identify sample characteristics from different individuals. These and other applications and approaches are readily implemented using the approaches and arrangements discussed herein.

Various example embodiments of the present invention are also directed to the integration of sample preparation/presentation structures with semiconductor optoelectronics and/or high-speed micro-optic detection circuits, and data processing and storage components in an effort to reduce the system size, reduce manufacturing cost, and increase parallelism, portability and robustness. According to one embodiment, the sample preparation/presentation structures are arranged on one substrate in close proximity to a semiconductor optoelectronics and/or high-speed micro-optic detection circuit, and data processing and storage components. According to another embodiment, the sample preparation/presentation structures are arranged in close proximity to the semiconductor optoelectronics and/or high-speed micro-optic detection circuits, and data processing and storage components all arranged on a single integrated circuit chip substrate.

According to a general example embodiment, a pyrosequencing microcircuit of the present invention includes one or more integrated photodetector(s) arranged in a planar array to affect a one-sided sensing architecture, with associated signal amplification, digitization, storage and processing circuits all fabricated on a single integrated circuit chip substrate. Micro-optic detectors are used for collection of the emitted signal. The signal amplification/processing circuitry is used to collect, analyze and readout the signal generated at the detectors and perform additional analog and/or digital signal processing. According to another configuration of the present invention, at least a portion of the processing circuits are arranged on an integrated circuit chip substrate apart from the sensing architecture.

For general information regarding sample analysis and for specific information regarding approaches that may be implemented in connection with one or more example embodiments of the present invention, reference may be made to the following U.S. Pat. No. 6,210,891 issued on Apr. 3, 2001 to Nyren et al. and entitled "Method of Sequencing DNA;" U.S. Pat. No. 6,258,568 issued on Jul. 10, 2001 to Nyren and entitled "Method of Sequencing DNA Based on the Detection of the Release of Pyrophosphate and Enzymatic Nucleotide Degradation;" U.S. Pat. No. 6,040,138 issued on Mar. 21, 2000 to Lockhart et al. and entitled "Expression Monitoring By Hybridization to High Density Oligonucleotide Arrays;" and U.S. Pat. No. 6,274,320 issued on Aug. 14, 2001 to Rothberg et al. and entitled "Method of Sequencing a Nucleic Acid." Each of the above-mentioned U.S. patents is fully incorporated herein, generally and specifically, by reference.

Turning now to the figures, similar components between the figures are similarly labeled to show at least a general level of correspondence of the illustrated components, with certain discussion thereof omitted for brevity.

FIG. 1 illustrates an assaying system 100 of the present invention, including a sample preparation structure 140 (e.g., micro-arraying device that spot samples for immobilization onto a substrate, microfluidic device or other dispensing structure), a processing circuit arrangement 150 and a man-machine interface arrangement 170. A first reservoir 105 contains one or more biological samples and is fluidly coupled to microcircuit arrangement 110 via one or more sample source channels 115. In turn, sample source channels are fluidly coupled to one or more test sites 120 formed on or in sample preparation structure 140 through sample source microchannels 122.

According to one example embodiment, sample preparation structure 140 is formed upon the same substrate used for processing circuit arrangement 150. Test sites 120 are formed upon the substrate, for example by etching. Additional details of the apparatus and techniques associated with the sample preparation device are set forth below. One of a plurality of test sites 120 is illustrated for brevity, with a variety of such test sites being applicable to this and other implementations.

A second reservoir 130 containing one or more reagents, such as enzymes, is fluidly coupled to microcircuit arrangement 110 by way of one or more reagent source channels 132a, 132b and 132c, which are respectively fluidly coupled to test sites 120 via reagent source microchannels 134a, 134b and 134c respectively. Second reservoir 130 is alternately implemented as a plurality of individual reagent-specific reservoirs, the quantity of which depends on the number and types of reagents necessary to supply all of the expected assays occurring on microcircuit arrangement 100 for specific implementations. First and/or second reservoirs are optionally located on microcircuit arrangement 110, and in particular integral to sample preparation structure 140.

Sample preparation device 140 is arranged and configured such that each test site thereof is in close proximity to a sensor array portion 155 of an assay and detection arrangement 160. The sample preparation device 140 and sensor array 155 are effectively communicatively coupled. A significant portion of light generated or originating at a test site 120 is observable at sensor array 155. Sensor array 155 is shown as being within sample preparation device 140 for illustrative purposes to demonstrate the proximity between sensor array 155 and a corresponding test site 120.

Processing circuit arrangement 150 includes assay and detection arrangement 160 and analysis arrangement 180. Assay and detection structure 160 includes one or more 2-dimensional image sensor arrays 155 as well as additional supporting control and logic circuitry. According to one embodiment, a 2-dimensional image sensor array 155 is associated with a plurality of test sites 120, a portion of sensor array 155 corresponding to a particular test site. According to another embodiment, processing circuit arrangement 150 includes a plurality of 2-dimensional image sensor arrays 155, each 2-dimensional image sensor array 155 corresponding with one of a plurality of test sites 120. Further, processing circuit arrangement 150 includes some combination of one or more 2-dimensional image sensor arrays corresponding with one or more test sites.

Processing circuit arrangement 150 is communicatively coupled to a man-machine interface (MMI) arrangement 170 by at least a control channel 172 and a data channel 174. The MMI arrangement 170 is an interface for communicating control information to microcircuit arrangement 110, and for communicating information from the microcircuit arrangement 110 to a user. In one implementation, the MMI arrangement 170 includes an external computing arrangement having a keyboard for control information input and a monitor for displaying information to a user. However, the MMI arrangement 170 can also be implemented in a variety of other conventional configurations including, but not limited to visual displays, audio interfaces, indicator lights, and other communications devices. The MMI arrangement 170 may be configured remote from microcircuit arrangement 110; however, the MMI arrangement may also be incorporated in, on or coupled to microcircuit arrangement 110 as the application of assaying system 100 dictates for user convenience. Data communicated from microcircuit arrangement 110 can include an image representative of one or more assays, or diagnostic type information such as from a look-up table responsive to assay information.

Figure 2:
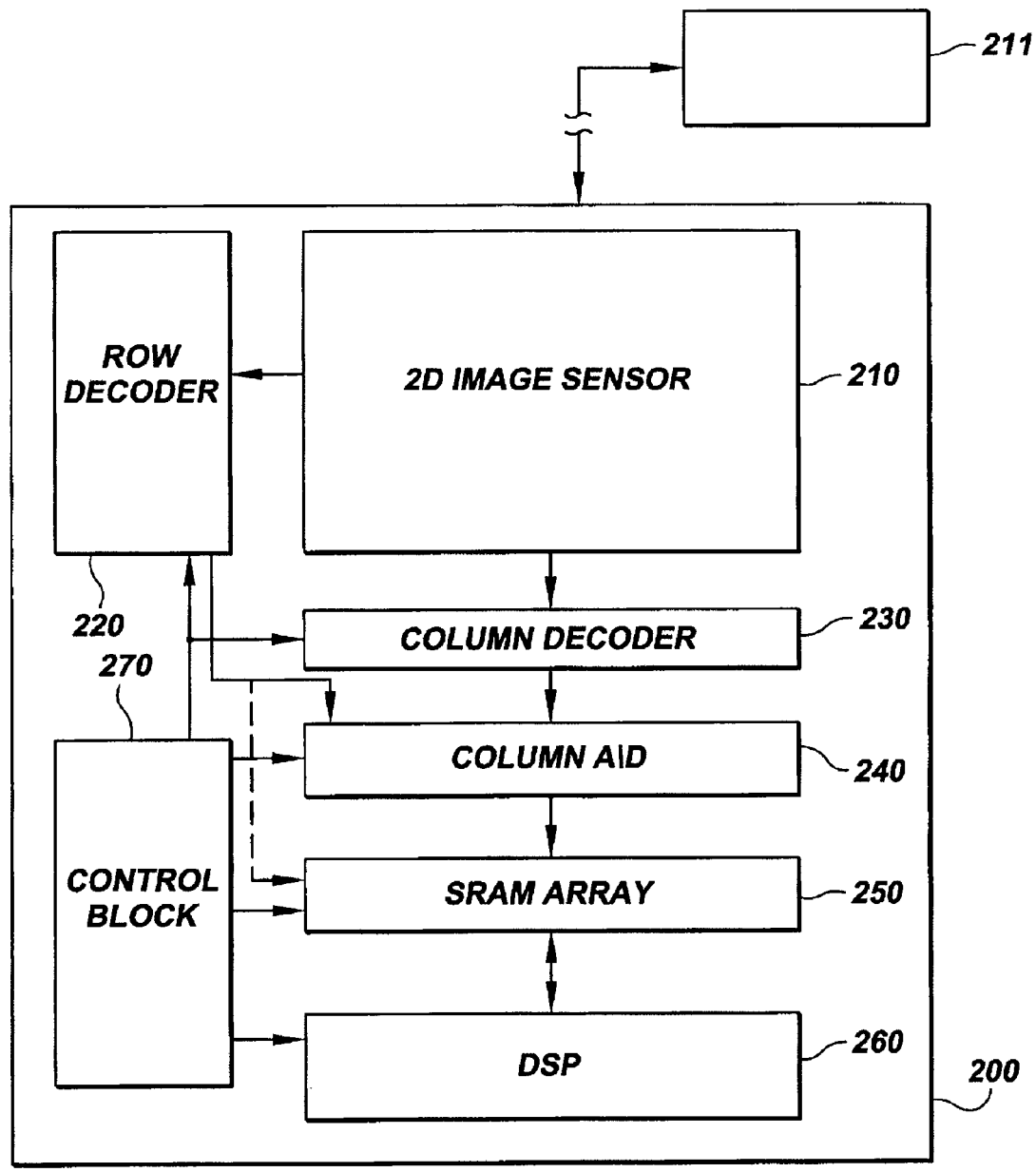
FIG. 2 is a block diagram illustrating detection and processing portions of a microcircuit arrangement, according to another example embodiment of the present invention.

FIG. 2 is a block diagram illustrating a processing circuit arrangement 200. Processing circuit arrangement 200 is similar in function to processing circuit arrangement 150 of FIG. 1; however, boundaries between assay and detection, and analysis portions are implemented in a variety of manners, depending upon the implementation. For instance, these portions may be indistinguishable in some implementations of the present invention. In addition, the processing circuit arrangement 200 can be implemented using a variety of platforms, such as a CMOS platform with the indicated components integrated on a single semiconductor chip.

The processing circuit arrangement 200 includes at least one 2-dimension image sensor 210 comprising a sensor array of pixel photodetectors generally arranged in a matrix of rows and columns. Two-dimension image sensor 210 is communicatively coupled to a row decoder 220 and a column decoder 230, which may be implemented, for example, in a manner as described in the referenced Appendices. Column decoder 230 is further communicatively coupled to column analog-to-digital converters (column A/D) 240. The digital side of column A/D 240 is coupled to a fast-access memory arrangement 250, e.g., SRAM, cache memory or other high-speed electronic memory, which is communicatively coupled to a digital signal processor (DSP) 260. Control circuitry 270 is communicatively coupled to each of the components of processing circuit arrangement 200 as shown in FIG. 2 to control the operation of and the information flow between the components.

In another implementation, a temperature controller 211 controls the temperature of the 2D image sensor 210. The temperature controller 211 is implemented using one or more of a variety of devices, depending on the application. In one instance, the temperature controller 211 includes a temperature-controlled enclosure around the entire processing circuit arrangement 200. In another instance, the temperature controller 211 includes a peltier or other electronic cooling arrangement that is arranged to draw heat from the 2D image sensor 210. In still another instance, the temperature controller 211 is adapted to pass heating and/or cooling fluid for heat transfer with the 2D image sensor.

Figure 3:
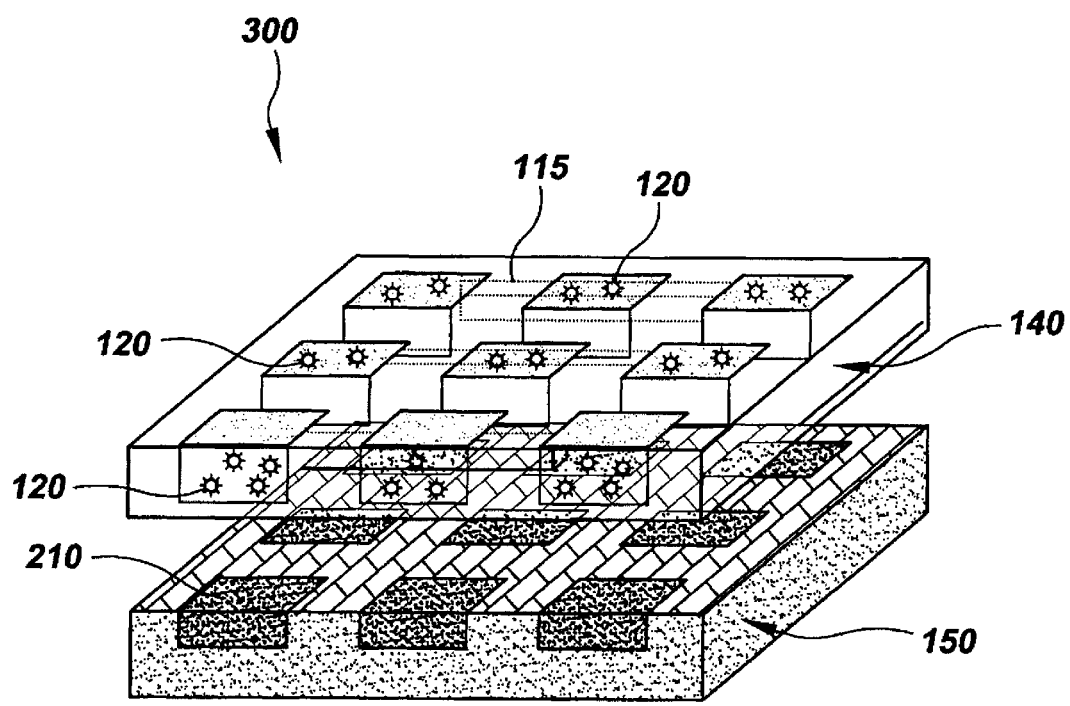
FIG. 3 is a perspective view of selected portions of a microcircuit arrangement, according to another example embodiment of the present invention.

FIG. 3 is a perspective physical view of a 3-dimensional configuration for a microcircuit assaying arrangement 300, according to another example embodiment of the present invention, implemented using a single integrated circuit chip having integrated detection and analysis CMOS-based circuitry. With reference to the previously-presented figures, the microcircuit assaying arrangement 300 of FIG. 3 also includes sensor arrays 210 (FIG. 2), a sample preparation device 140 (FIG. 1), and the single integrated circuit chip implementing the processing circuit arrangement 150 (FIG. 1). Various ones of a plurality of test sites 120 are shown in FIG. 3, interconnected by microchannels and microwells for supplying biological samples to selected test sites. The microchannels and microwells can be used for reagent delivery, as previously discussed, and also for DNA confinement during sample illumination. Sensor arrays 210, each corresponding to at least one test site, are shown arranged on processing circuit arrangement 150 such that sensor arrays and corresponding test sites 120 are located in close proximity to one another in 3-dimensional space.

Figure 4A:
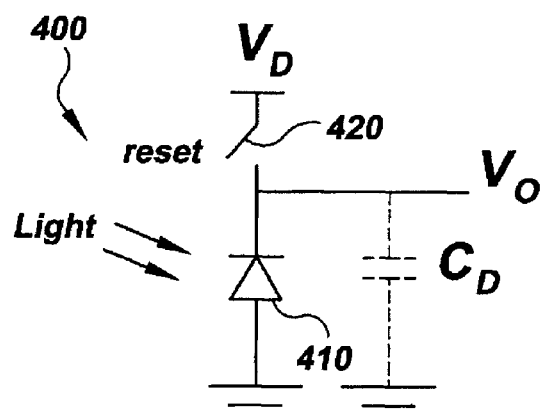
FIG. 4A is a schematic diagram illustrating a photodetector of a microcircuit arrangement, according to another example embodiment of the present invention.

FIG. 4A is a schematic diagram illustrating a photodetector for a microcircuit arrangement pixel, according to another example embodiment of the present invention. A 2-dimensional photodetector sensor array is formed of pixels 400, each pixel 400 including a photodiode 410. Photons incident on each photodiode 410 are converted to electrical charge (Q) which is accumulated (i.e., integrated) over diode capacitance ($C_D$). $C_D$ is not a discrete component, but rather an inherent property of implementing photodiode 410. The amount of charge collected is proportional to the light intensity and photon quantity incident on photodiode 410. The amount of charge can be "read" as an electrical voltage signal $V_O$ for each photodiode. A reset switch 420 (e.g., a transistor or other switchable semiconductor device) provides a control mechanism bringing $C_D$ to a known state.

Figure 4B:
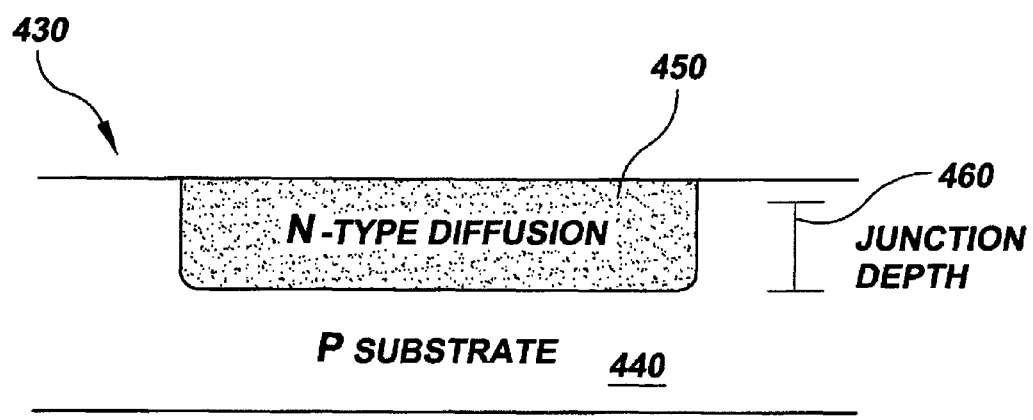
FIG. 4B is a cross section of a CMOS-based light detector, according to another example embodiment of the present invention.

FIG. 4B illustrates a cross section of a CMOS-type photodetector element (photodiode) 430. According to one example of the present invention, photodiode 430 is optimized for detecting a specific wavelength of light that a biological assay is expected to generate. A P-type substrate 440 includes an N-type diffusion doping region 450. In one implementation, an N-type diffusion doping region 450 has a dopant concentration and a junction depth 460 that are selected to optimize the charge response of the photodiode to light for the specific wavelength of the biological assay.

In another particular implementation, the photodiode 430 is optimized to detect firefly light generation at a wavelength of about 560 nm. To achieve such detection, the photodiode is fabricated using a junction depth of about 3 micrometers and having a doping concentration of the N-type diffusion region 450 of approximately $5*10^{15}$ dopant species per $cm^3$. The P-type substrate 440 has a dopant concentration of about $10^{15}$ dopant species per $cm^3$.

In another example embodiment of the present invention, noise reduction circuitry is implemented with a CMOS-type photodetector. For example, referring again to FIGS. 3 and 4B, one or more sensors in the sensor array 210 can be implemented with a CMOS type photodetector, such as photodiode 430. In this example, the processing circuit arrangement 150 includes on-chip circuitry adapted to reduce non-ideal characteristics of signals generated by the CMOS-type photodetector. Such non-ideal characteristics include, for example, thermally-generated noise and shot noise. By removing noise components of the signals, the remaining portion of the signals more accurately represent the light received by the CMOS-type photodetector (photodiode 430).

In one implementation, background subtraction circuitry is included on-chip with the processing circuit arrangement 150 and is adapted to reduce deterministic thermally-generated portions of signals produced by the photodiode 430. Thermal-related noise is subtracted out of the signal, leaving behind a signal that more accurately represents light detected at the photodiode 430. In addition, once the deterministic thermally-generated portion of the signals has been removed, remaining portions of the signal that are attributed to noise can be removed using other approaches.

In another implementation, signal averaging circuitry is included with the processing circuit arrangement 150. The signal averaging circuitry may, for example, be used independently from or in conjunction with the background subtraction circuitry discussed above. The signal averaging circuitry is adapted to reduce noise in the signals generated by the photodiode 430 by lowering independent noise components by the square root of the number of independent samples taken. Such independent noise components that can be reduced include shot noise (having a variance equal to the square root of its mean) that is not typically removed using other noise-reduction approaches, such as background subtraction. For example, in one instance where the signal averaging circuitry is implemented with the background subtraction circuitry, signal averaging is used to reduce a shot noise component that remains after background subtraction.

Figure 5:
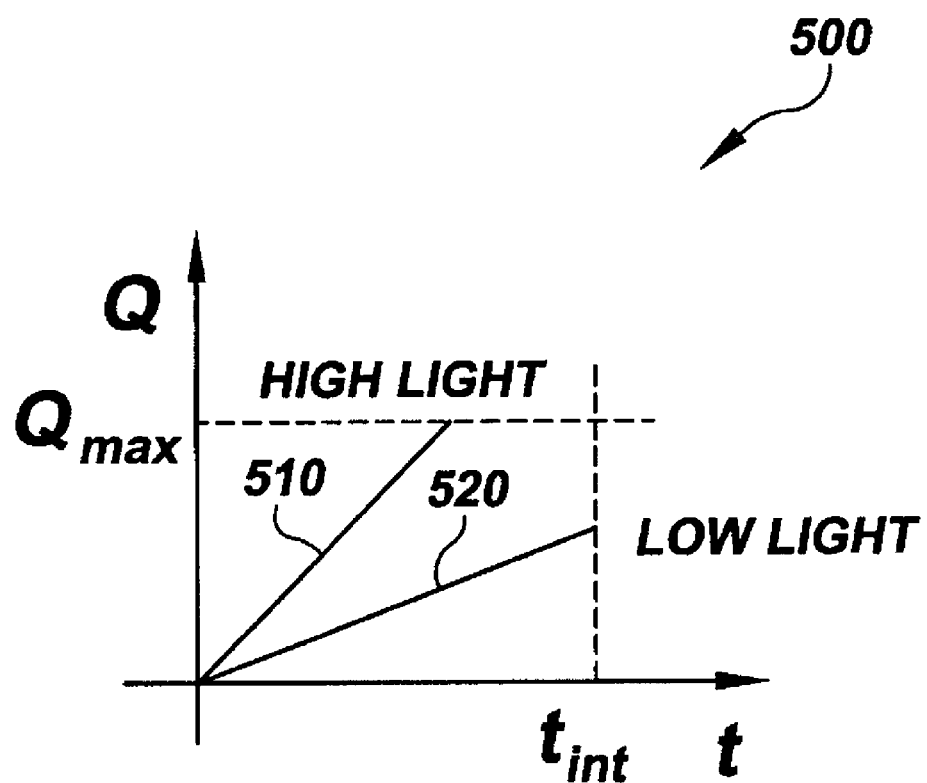
FIG. 5 is a graph illustrating the electrical response of a photodetector, according to another example embodiment of the present invention.

In another example embodiment of the present invention, FIG. 5 shows plots 510 and 520 of an electrical response of a photodetector over time. The plots may, for example, be achieved using the approaches shown in FIGS. 4A and 4B. The plot 510 shows accumulated charge (Q) for relatively high light incident on a photodetector (e.g., photodetector 410 of FIG. 4A), and plot 520 shows Q for relatively low light incident upon the photodetector.

Figure 6A:
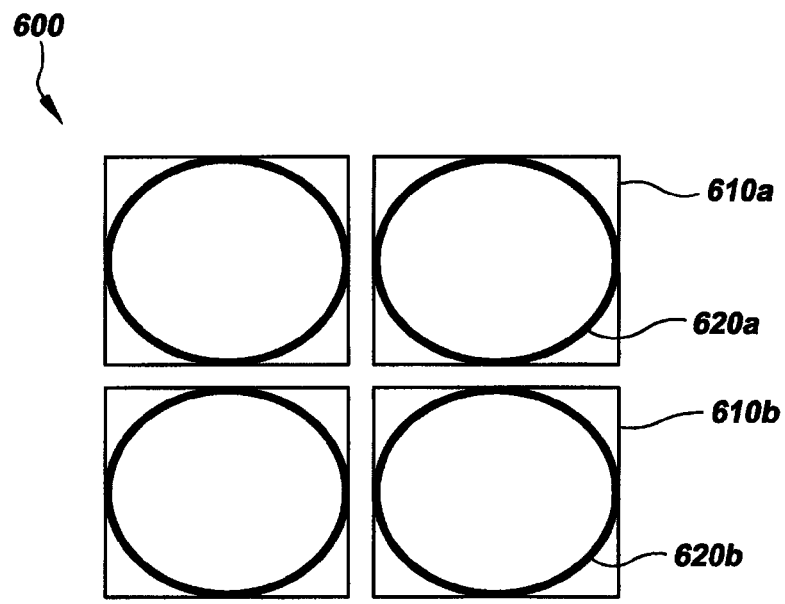
FIG. 6A illustrates an assay sensor array configuration utilizing a single pixel per assay test site, according to another example embodiment of the present invention.

In connection with another example embodiment of the present invention, FIG. 6A shows an assay sensor array 600 configuration utilizing a single pixel (e.g., 610a, 610b) oriented per assay test site (e.g., 620a, 620b) respectively. Light detected at the single pixel is used as data for the particular assay test sight. For instance, when light from assay test sight 620a reaches pixel 610a, characteristics of the light cause the pixel 610a to generate an electrical response, such as by accumulating charge as discussed in connection with FIG. 5 above. The response is then used to detect a characteristic of the material being assayed.

Figure 6B:
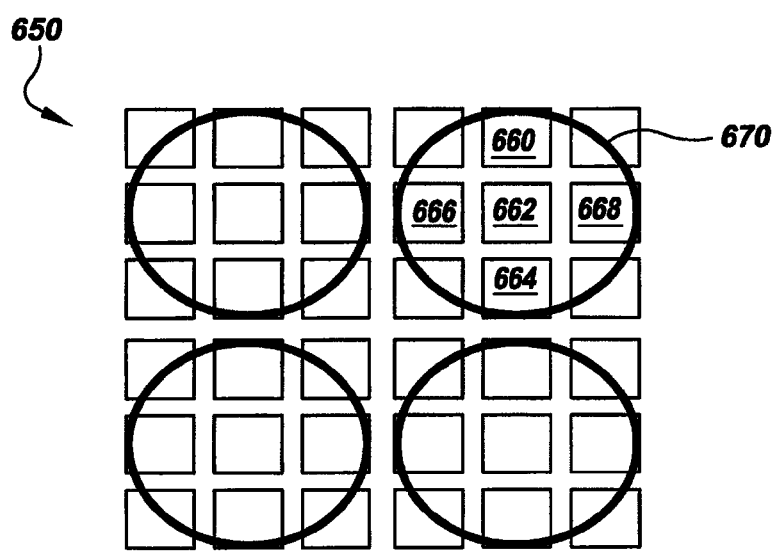
FIG. 6B illustrates an assay sensor array configuration utilizing a plurality of pixels per assay test site, according to another example embodiment of the present invention.

FIG. 6B illustrates an assay sensor array 650 configuration utilizing a plurality of pixels 660-668 oriented per assay test site 670, according to another example embodiment of the present invention. In this example, relative to FIG. 6A, more pixels are used per assay test site and can correspondingly be used to detect a more detailed response from material at the test site. For instance, different ones of the pixels can be used for detecting different characteristics, such as by using a filter with particular pixels for filtering out a specific wavelength or wavelength range of light. In one implementation, the size of the test sites and/or the digital pixels is programmable, for instance, such that a portion (e.g., a block) of the plurality of pixels 660-668 is used for a particular assay.

Figure 7:
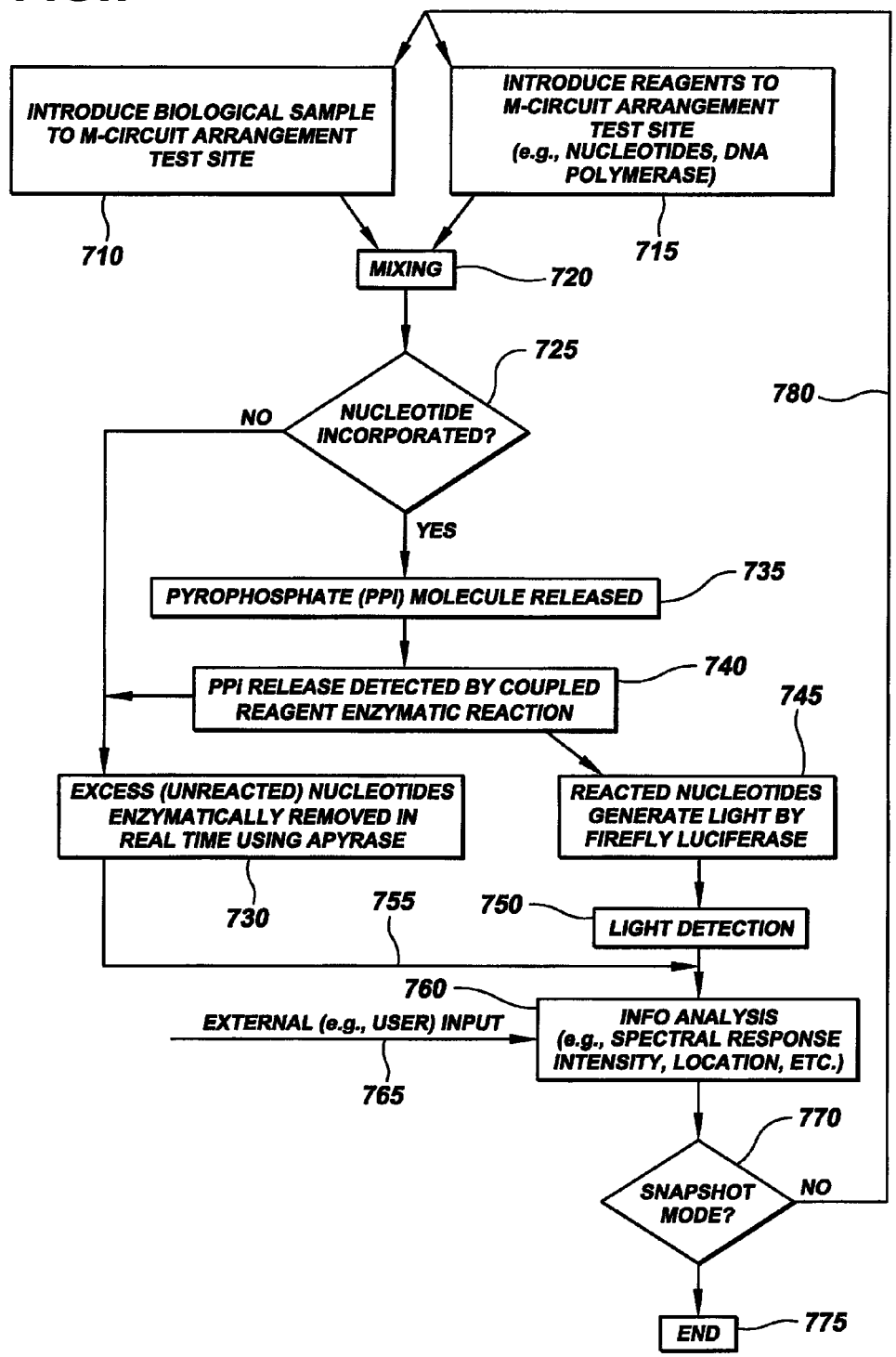
FIG. 7 is a flow chart illustrating a pyrosequencing approach using a microcircuit arrangement, according to another example embodiment of the present invention.

FIG. 7 is a flow chart illustrating a pyrosequencing approach using a microcircuit arrangement, according to another example embodiment of the present invention. The following approach may be implemented, for example, using one or more of the microcircuit arrangements discussed herein. At step 710, a biological sample is introduced to a test site of a microcircuit arrangement, for example, from a reservoir. Similarly, one or more reagents such as a known nucleotide, DNA polymerase or other chemical used to drive pyrosequencing reactions is introduced at step 715 to the test site. The biological sample and reagents are mixed at step 720, e.g., using mechanical, electrical, dissolution and/or magnetic methods. A chemical reaction between the biological sample under test and the reagent is effected at step 725.

In some instances where one or more reagent is not incorporated, excess (i.e., unreacted) reagent is enzymatically removed in real time using, for example, apyrase at step 730. The lack of incorporation of a particular reagent such as nucleotide is optionally factored in, at step 755, and an information analysis is implemented at step 760. Conditions and/or detection techniques employed in further assays are modified in response to such lack of incorporation.

If an introduced nucleotide reagent is incorporated, pyrophosphate (PPi) molecules are released at step 735 and detected at step 740 by a coupled reagent enzymatic reaction that generates light at step 745 by firefly luciferase. A sensor array comprising digital pixels having photodiodes, and corresponding to the test site, detects the generated light at step 750 by accumulating charge across the photodiode. The accumulated charge (Q) is proportional to the characteristics of the light incident on the photodiode and the photodiode's response properties. Charge from the various pixels of the sensor array are sampled and respectively converted substantially in parallel to a digital single responsive to the respective pixel charge. The digital signals are optionally further analyzed at step 760, either directly or by first storing the signals in a memory arrangement for subsequent analysis. In one implementation, the digital signals are stored in a memory arrangement on a common chip substrate with the sensor array.

Analysis of the digital signals derived from the sensor array corresponding to a particular test site is performed in a variety of manners, and can include any combination of digital visual image processing. For instance, as is known in the digital camera and other fields, processing involving pan, tilt and zoom functions can be accomplished electronically. Other signal characteristics such as intensity, magnitude or total light energy (e.g., photon quantity and/or strength) are optionally processed for determination of characteristics of the sample being analyzed. Other analysis approaches that may be implemented include spectral, wavelength and/or frequency analysis including component determinations; light generation response as a function of test site geography; and determination of assertion and/or non-assertion of selected combinations of digital pixels having differing characteristics or sensitivities with respect to combinations of interest stored in a look-up table or other relational database. In one implementation, such information analysis incorporates external input at step 765.

After information analysis at step 760, the assay optionally continues, for example, if additional reagents (e.g., nucleotides) are implemented. Alternately, the assay stops at step 775 for a particular test site, for example, when a snapshot mode (i.e., one-time analysis) is selected. However, the results of assays at various test sites can be incorporated into the processes of other assays, for example, to modify the need, speed or technique of a subsequent assay.

Figure 8:
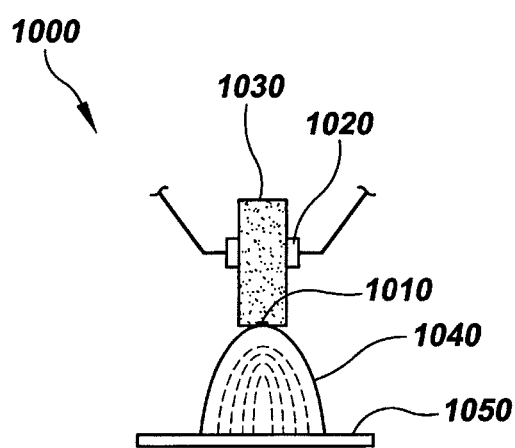
FIG. 8 is a block diagram illustrating a pyrosequencing arrangement including a CCD imager and ultrasonic sprayer for modeling a microcircuit arrangement, according to an example embodiment of the present invention.

FIG. 8 is a block diagram illustrating a pyrosequencing arrangement including an imager (e.g., a CCD or a light detection arrangement as discussed above) and ultrasonic sprayer for modeling a microcircuit, according to an example embodiment of the present invention. The pyrosequencing arrangement 1000 is a platform for DNA analysis. Arrangement 1000 includes an ultrasonic sprayer (e.g., a piezoelectric sprayer such as a Microjet Drop on demand dispenser from Microfab, Inc.) 1010, a robotic arm 1020 (e.g., a Beckman Biomek 2000; 1000 armdroid 100 robotic arm made by D&M Computing) and an integrated imaging system 1030 having the imager. Piezoelectric sprayer 1010 is dipped into a nucleotide solution upon which a thin film of solution is formed.

The nucleotide 1040 is sprayed onto a CMOS-based DNA-array 1050. Incorporation of a nucleotide includes a light-generating reaction. The generated light is emitted proportional to the extent of incorporation, and subsequently available to the integrated imaging system 1030 for detection. The single sprayer 1010 is used for delivery of a plurality of different nucleotides in sequence. According to one method of the present invention, four different nucleotides are delivered using the single sprayer 1010. Sprayer 1010 is washed by dipping it in a water solution and using ultrasonication of the nozzle in the water solution.

As discussed above, samples can be prepared and provided for analysis using a variety of manners, known and otherwise, and implemented in connection with the detection approaches discussed herein. In one particular implementation, a light detection arrangement facilitates the detection of molecules such as chemicals, organisms, genes, DNA or portions thereof. Various approaches in connection with this implementation involve certain features, and may be implemented in various applications as further described in connection with the following U.S. Patents: U.S. Pat. No. 5,846,708 issued on Dec. 8, 1998 to Hollis et al. and entitled "Optical and Electrical Methods and Apparatus for Molecule Detection," U.S. Pat. No. 5,965,452 issued on Oct. 12, 1999 to Kovacs and entitled "Multiplexed Active Biological Array," and U.S. Pat. No. 6,379,897 issued on Apr. 30, 2002 to Weidenhammer et al. and entitled "Methods for Gene Expression Monitoring on Electronic Microarrays," as well as certain improvements to various features described further below. Each of the above-mentioned U.S. patents is fully incorporated herein for general discussion of approaches and arrangements and for specific discussion of approaches and arrangements that may be implemented in connection with one or more example embodiments.

As mentioned above, any of variety of sample-dispensing structures may be used for sample preparation. In one implementation, a microfluidic device for providing a sample for analysis includes a plurality of micro-reservoirs, connecting microchannels and assaying test sites formed into a substrate, for example, by etching. The plurality of micro-reservoirs, along with the connecting microchannels and assaying test sites of the microfluidic device, are adapted to facilitate delivery of biological samples, as well as other reagents such as enzymes, chemicals, and mixtures appropriate for particular assays, to designated test sites. For general information and various implementations of such devices, and for specific information regarding such devices and approaches to which one or more example embodiments of the present invention may be applicable, reference may be made to U.S. Pat. No. 5,603,351 issued on Feb. 18, 1997 to Cherukuri et al. and entitled "Method and System for Inhibiting Cross-Contamination In Fluids of Combinational Chemistry Device," and U.S. Pat. No. 6,440,722 issued on Aug. 27, 2002 to Knapp et al. entitled "Microfluidic Devices and Methods for Optimizing Reactions."

In another example embodiment of the present invention, a photodetector element, such as discussed above, is shaped to match an assay geometry. The shaping and matching is implemented, for example, to effect one or more of: an increase in detection sensitivity, a reduction in inter-assay interference and the provision of a close interaction between the chemistry and microcircuits. According to one aspect, the size of a test site or of a sensor array of pixel photodetectors associated with a test site, or of the individual pixel photodetectors can be increased or decreased to best fit an intended purpose of the respective test site. For example, one or more photodetectors can be associated with a corresponding test site as discussed in connection with FIG. 6B above. Furthermore, photodetectors associated with a corresponding test site can be all of one photodetector type to achieve fine geographic or intensity resolution of the generated light across the test site. Alternatively, photodetectors associated with a corresponding test site are selected to include two or more types of photodetectors having, for example, different sensitivities and light response characteristics for measuring a variety of differing characteristics at a particular test site. For instance, photodetectors having color (i.e., electromagnetic radiation frequency response), intensity, direction, polarization, heat, radiation, pressure, or other characteristics may be implemented.

In another implementation, multicolor differentiation across a sample is effected using a plurality of different types of photodetectors arranged in a repetitive pattern in a sensor array. An approach similar to the pattern of red, green and blue-specific pixels arranged in a typical digital image display can be implemented to achieve this end. In other implementations, photodetectors are arranged in a sensor array corresponding to criteria such as particular fluid dynamics, mixing efficiencies, reaction times across a test site, or other test site geographic considerations.

In a more particular implementation, photodetectors in a sensor array are differentiated based on sensitivity related to the detection of a particular physical characteristic of a sample. In one example, a first "type" of pixel photodetector arranged within a sensor array measures light intensity on a coarse scale. A second "type" of pixel photodetector arranged within the sensor array is configured to measure light intensity on a finer scale confined to a portion of the coarse scale measured by the first "type" pixel photodetector. In this manner, the first type of pixel photodetector can be used to isolate a particular response and an appropriate set of finer pixel photodetectors can be used to improve accuracy of light measurement within the coarse scale.

In another example configuration, a sensor array includes sets of photodetector "types" sensitive to overlapping or adjacent ranges of light. A digital signal processing arrangement is used to detect that the detected light passes from one adjacent/overlapping scale to a next incrementally higher or lower scale, thereby detecting the reduction or increase of light intensity. Although the different "types" of photodetectors may all measure the same physical characteristic, they may do so according to various constraints, sensitivities and parameters. The above-described scaled approach to arrangement of photodetectors within a sensor array may also be applied to other light features such as frequency (i.e., color).

In another example embodiment of the present invention, a light detection arrangement including a sensor array of photodetectors, such as described above, is adapted to selectively power and/or process data from the photodetectors. For example, where coarse scale and fine scale photodetectors are in the array, one type of the coarse and fine scale photodetectors can be selectively powered/processed. When starting with a coarse scale detection, digital signal processing algorithms are used to determine that photodetectors sensitive to a finer scale should be powered and/or processed, once a coarse scale characteristic is detected. Similarly with a sensor array arrangement of photodetectors having overlapping or adjacent sensitivity ranges, a digital signal processing algorithm can be used to track a particular characteristic of interest as it changes from range to range by powering, enabling, interrogating or processing photodetector(s). With this approach, those photodetectors not in use need not consume power or valuable processing time, thereby speeding up processing of more relevant photodetectors.

According to another aspect of the present invention, relevancy determinations are implemented utilizing multiple assay test sites. Relevancy determinations based on time are one example. Digital signal processing is used to dynamically modify the assay process at a second test site, conducted later in time and responsive to an assay at a first test site conducted prior in time. According to a more particular example, a first assay occurs first in time at a first test site. Based on the results of the first assay to classify in some manner the sample being assayed, the process, technique, method, mixture, or other characteristic of a second assay is dynamically modified responsive to the results of the first assay. The classification can be positive (i.e., the first assay ascertains that the assay sample is included in a particular set of outcomes), or can be negative (i.e., the first assay ascertains that the assay sample is excluded from a particular set of outcomes). Using approaches as discussed above, the type or operation of photodetectors can be selectively tailored to effect these and other relevancy determinations.

One method for implementing relevancy determinations is by applying assay results, either intermediate or "final," to a look-up table of possible results located, for example, in memory. Other conventional decision analysis techniques, such as decision tree analysis, fuzzy logic, or other methods can also be implemented for processing digital signals derived from the sensor array pixels.

According to another aspect of the present invention, relevancy determinations are implemented utilizing information extrinsic to an assaying process. One example of extrinsic information used to make relevancy determinations for subsequent assaying process is user input. A user can select or input one or more variables affecting an assay relevancy determination. For example, a user might make an initial classification of a biological sample and provide such classification information to a light detection arrangement, such as those discussed above. The initial classification is used to conduct, monitor or use the results of particular assays utilizing particular test sites, photodetectors of sensor arrays or reagent mixtures and ignoring other test sites. In this manner, processing speed is increased by focusing or prioritizing the processing power to the most relevant assays or assay characteristics. In addition, such user input can also be provided at some intermediate point in an assaying process, for example, in response to human evaluation of intermediate results.

In a variety of implementations, one or more of the approaches discussed herein are implemented using processing compensation for producing data that more accurately represents characteristics of the samples being assayed. For instance, when digital images are captured and/or displayed, a processor sharing a common chip or substrate with a light detection circuit as discussed herein has been found particularly useful for implementing a wide variety of compensation techniques. This compensation may be useful for countering external "noise" effects commonly found with previously-available light detection circuits. Additional customization is achieved through customization of a sensor array (i.e., hardware customization). Thereby, microcircuit arrangements of the present invention for assaying biological samples can be uniquely customized for various biological assaying applications including, for example, bio-sensing; diagnosis; animal husbandry; and plant genetic engineering.

For background information on photodetectors and processing of signals therefrom, reference may be made to U.S. Pat. No. 5,461,425 issued on Oct. 24, 1995 to Fowler et al. and entitled "CMOS Image Sensor With Pixel Level A/D Conversion," U.S. Pat. No. 5,801,657 issued on Sep. 1, 1998 to Fowler et al. and entitled "Serial Analog-To-Digital Converter Using Successive Comparisons," U.S. Pat. No. 6,310,571 issued on Oct. 30, 2001 to Yang et al. and entitled "Multiplexed Multi-Channel Bit Serial Analog-To-Digital Converter," and U.S. Pat. No. 6,380,880 issued on Apr. 30, 2002 to Bidermann and entitled "Digital Pixel Sensor With Integrated Charge Transfer Amplifier." Each of the above-mentioned U.S. Patents is fully incorporated herein, generally and specifically, by reference.

Other implementations and approaches of the present invention are directed to certain features, and may be implemented in various forms and applications as further described in one or any combination of the three attachments to the underlying and above-referenced U.S. Provisional Application, including Appendix 1, Appendix 2 and Appendix 3. The foregoing documents are fully incorporated herein, generally and specifically, by reference.

While the present invention has been described with reference to several particular example embodiments, those skilled in the art will recognize that many changes may be made thereto without departing from the spirit and scope of the present invention. The present invention is applicable to a variety of sensor implementations and other subject matter, in addition to those discussed above.

What is claimed is:

1. An apparatus comprising:
an integrated circuit chip configured and arranged as a one-sided biological sensing architecture that includes
a substrate of the integrated circuit chip having a first side;
a plurality of test sites that are recessed into the first side of the integrated circuit chip substrate and configured and arranged in a planar array;
a plurality of photodiodes that are integrated into the recesses of the plurality of test sites and that are configured and arranged with a diffusion doping region having a dopant concentration and junction depth sufficient to detect firefly luciferase light produced during a pyrosequencing reaction within the plurality of test sites and generated from a sample contained within the test sites;
an analog to digital converter circuit fabricated as part of the integrated circuit chip and configured and arranged to convert analog voltages from the plurality of photodiodes into digital values; and
a memory circuit configured and arranged to store the digital values and that is fabricated as part of the integrated circuit chip.

2. The apparatus of claim 1, wherein the substrate is a P-type substrate and wherein the plurality of photodiodes each include an N-type diffusion doping region that has the dopant concentration and junction depth sufficient to detect firefly luciferase light produced during a pyrosequencing reaction within the test sites, wherein the P-type substrate has a first dopant concentration of a first dopant species per $cm^3$ and the N-type diffusion region has a second dopant concentration of a second dopant species per $cm^3$ and wherein a ratio between the first dopant concentration and the second dopant concentration is sufficient to detect firefly luciferase light produced during a pyrosequencing reaction.

3. The apparatus of claim 1, wherein the substrate is a P-type substrate and wherein the plurality of photodiodes each include an N-type diffusion doping region that has the junction depth sufficient to detect firefly luciferase light produced during a pyrosequencing reaction within the test sites and wherein the junction depth is at least about 3 micrometers.

4. The apparatus of claim 1, further including processing circuitry that is configured and arranged to reduce non-ideal characteristics of signals generated by the plurality of photodiodes and that is fabricated as part of the integrated circuit chip.

5. The apparatus of claim 1, further including processing circuitry adapted to reduce thermally-generated noise in signals generated by the plurality of photodiodes and that is fabricated as part of the integrated circuit chip.

6. The apparatus of claim 1, further including signal averaging circuitry that is configured and arranged to lower shot noise for individual photodiodes of the plurality of photodiodes by averaging inputs from the plurality of photodiodes.

7. The apparatus of claim 1, further including one or more reset switches configured and arranged to reset the plurality of photodiodes to a known state.

8. The apparatus of claim 1, wherein the planar array includes a plurality of columns and rows and wherein the apparatus further includes column and row decoder circuits that are configured and arranged to address a photodiode corresponding to each test site.

9. The apparatus of claim 1, further including processing circuitry that is configured and arranged to process input from each test site as a pixel of a plurality of pixels.

10. The apparatus of claim 9, wherein the processing circuitry is further configured and arranged to process data from the pixels in groups corresponding to different detected characteristics.

11. The apparatus of claim 10, further including at least one filter for a particular group of pixels, the filter being configured and arranged to filter out a specific wavelength of light.

12. The apparatus of claim 1, further including circuitry for sampling charge from the plurality of photodiodes in parallel to produce a digital signal.

13. The apparatus of claim 1, further including a plurality of channels that are fluidly coupled to the plurality of test sites and that are configured and arranged to deliver reagents to the plurality of test sites.

14. An apparatus comprising:
an integrated circuit chip configured and arranged as a one-sided biological sensing architecture that includes
a substrate of the integrated circuit chip having a first side;
a plurality of test sites that are recessed into the first side of the integrated circuit chip substrate and configured and arranged in a planar array;
a plurality of photodiodes that are integrated into the recesses of the plurality of test sites and that are configured and arranged with a diffusion doping region having a dopant concentration and junction depth sufficient to detect firefly luciferase light produced during a pryosequencing reaction within the plurality of test sites and generated from a sample contained within the test sites;
an analog to digital converter circuit fabricated as part of the integrated circuit chip and configured and arranged to convert analog voltages from the plurality of photodiodes into digital values;
a memory circuit configured and arranged to store the digital values and that is fabricated as part of integrated circuit chip; and
wherein the substrate is a P-type substrate with a dopant concentration of about $10^{15}$ dopant species per $cm^3$ and wherein the plurality of photodiodes each include an N-type diffusion with a dopant concentration of about $5*10^{15}$ dopant species per $cm^3$.

15. A method of detecting luciferase light generation, the method comprising:
providing a reagent to a plurality of test sites that are recessed into a first side of an integrated circuit chip substrate and that are arranged in a planar array;
measuring charge accumulation in a plurality of photodiodes that are integrated into the recesses of the plurality of test sites and that are configured and arranged with a diffusion doping region having a dopant concentration and junction depth sufficient to detect firefly luciferase light produced during a pyrosequencing reaction within the plurality of test sites and generated responsive to interaction between the reagent and test samples contained within the plurality of test sites;
converting the measured charge accumulation to a digital value using an analog to digital converter circuit that is fabricated as part of the integrated circuit chip substrate; and
storing the digital values in a memory circuit that is fabricated as part of the integrated circuit chip substrate.

16. The method of claim 15, further including a step of reducing shot noise from individual photodiodes of the plurality of photodiodes by averaging inputs from the plurality of photodiodes using signal averaging circuitry.

17. The method of claim 15, wherein the step of converting the measured charge accumulation to a digital value is accomplished by sampling charge from the plurality of photodiodes in parallel.

18. The method of claim 15, wherein the reagent is dNTP and the test samples are DNA sequences.

* * * * *